US012685558B2

(12) United States Patent (10) Patent No.: US 12,685,558 B2
Howell (45) Date of Patent: Jul. 21, 2026

(54) SKIN NICKING DEVICE FOR CATHETER PLACEMENT SYSTEM

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 509 days.

(21) Appl. No.: 18/109,793

(22) Filed: Feb. 14, 2023

(65) Prior Publication Data

US 2023/0255660 A1     Aug. 17, 2023

Related U.S. Application Data

(60) Provisional application No. 63/310,531, filed on Feb. 15, 2022.

(51) Int. Cl.
   *A61B 17/3209* (2006.01)
   *A61B 17/34* (2006.01)
(52) U.S. Cl.
   CPC .... *A61B 17/32093* (2013.01); *A61B 17/3415* (2013.01); *A61B 17/3496* (2013.01)
(58) Field of Classification Search
   CPC .......... A61B 17/32093; A61B 17/3415; A61B 17/3496
   See application file for complete search history.

(56) References Cited

U.S. PATENT DOCUMENTS 2,566,499 A   9/1951  Richter
2,842,133 A   7/1958  Antoni 3,921,631 A   11/1975  Thompson
4,324,044 A    4/1982  Shahinian, Jr.
4,392,856 A    7/1983  Lichtenstein
4,601,710 A    7/1986  Moll
            (Continued)

FOREIGN PATENT DOCUMENTS

CN      2456639 Y    10/2001
CN   210844555 U     6/2020
            (Continued)

OTHER PUBLICATIONS

PCT/US2021/059256 filed Nov. 12, 2021 International Search Report and Written Opinion dated Mar. 23, 2022.
            (Continued)

*Primary Examiner* — Ashley L Fishback
(74) *Attorney, Agent, or Firm* — Rutan & Tucker LLP

(57)     ABSTRACT

A catheter placement system including a catheter, a needle for creating an insertion site, and a skin nicking device for enlarging the insertion site. A catheter placement device includes the skin nicking device slidably coupled with the needle, where the skin nicking device has one or more blades attached to a frame thereof. Distally displacing the skin nicking device along the needle causes the blade to nick the skin to enlarge the insertion site. A shield of the skin nicking device transitions between a safe configuration encapsulating the blade and a use configuration exposing the blade and the shield may be biased toward the safe configuration. A latch secures the shield in the safe configuration and an actuator releases the latch. A sheath of the skin nicking device includes the needle slidably disposed within a lumen thereof and a sharp tip of the blade embedded within a wall thereof.

23 Claims, 15 Drawing Sheets

(56) References Cited

U.S. PATENT DOCUMENTS

| | | | |
|---|---|---|---|
| 4,693,250 | A | 9/1987 | Coons |
| 4,889,112 | A | 12/1989 | Schachner et al. |
| 4,955,890 | A | 9/1990 | Yamamoto et al. |
| 5,098,393 | A | 3/1992 | Amplatz et al. |
| 5,279,285 | A | 1/1994 | Griggs |
| 5,334,157 | A | 8/1994 | Klein et al. |
| 5,509,900 | A | 4/1996 | Kirkman |
| 5,578,009 | A | 11/1996 | Kraus et al. |
| 5,728,073 | A | 3/1998 | Whisson |
| 5,755,697 | A | 5/1998 | Jones et al. |
| 5,800,450 | A | 9/1998 | Lary et al. |
| 5,843,115 | A | 12/1998 | Morejon |
| 6,033,388 | A | 3/2000 | Nordstrom et al. |
| 6,517,519 | B1 | 2/2003 | Rosen et al. |
| 6,544,277 | B1 | 4/2003 | O'Heeron et al. |
| 6,761,725 | B1 | 7/2004 | Grayzel et al. |
| 9,114,227 | B2 | 8/2015 | Blanchard |
| 9,480,498 | B1 | 11/2016 | Kessler |
| 10,028,762 | B1 | 7/2018 | Slupchynskyj |
| 10,188,403 | B2 | 1/2019 | Mirochinik et al. |
| 10,376,675 | B2 | 8/2019 | Mitchell et al. |
| 10,603,071 | B1 | 3/2020 | Whitman et al. |
| 2002/0040231 | A1 | 4/2002 | Wysoki |
| 2002/0161387 | A1 | 10/2002 | Blanco |
| 2002/0165600 | A1 | 11/2002 | Banas et al. |
| 2002/0177864 | A1 | 11/2002 | Camrud |
| 2003/0074013 | A1 | 4/2003 | Schooler et al. |
| 2004/0133227 | A1 | 7/2004 | Shang et al. |
| 2004/0181246 | A1 | 9/2004 | Heppler |
| 2004/0181273 | A1 | 9/2004 | Brasington et al. |
| 2005/0177183 | A1 | 8/2005 | Thorne et al. |
| 2009/0024089 | A1 | 1/2009 | Levine et al. |
| 2009/0076435 | A1 | 3/2009 | Melsheimer et al. |
| 2009/0125030 | A1 | 5/2009 | Tebbe et al. |
| 2010/0057056 | A1 | 3/2010 | Gurtner et al. |
| 2012/0130417 | A1 | 5/2012 | Lepulu et al. |
| 2012/0226299 | A1 | 9/2012 | Heppler |
| 2013/0197558 | A1 | 8/2013 | Ingold, Jr. et al. |
| 2016/0128713 | A1 | 5/2016 | Rauchwerger et al. |
| 2016/0220786 | A1 | 8/2016 | Mitchell et al. |
| 2016/0346503 | A1 | 12/2016 | Jackson et al. |
| 2017/0128700 | A1 | 5/2017 | Roche Rebollo |
| 2017/0296792 | A1 | 10/2017 | Ornelas Vargas et al. |
| 2019/0307485 | A1 | 10/2019 | Kiev |
| 2019/0351183 | A1 | 11/2019 | Ishida |
| 2020/0061322 | A1 | 2/2020 | De Rezende Neto |
| 2020/0086095 | A1 | 3/2020 | Kleinhaus |
| 2020/0155190 | A1 | 5/2020 | Basadonna et al. |
| 2020/0222077 | A1 | 7/2020 | Takahashi |
| 2020/0246597 | A1 | 8/2020 | Broniec et al. |
| 2021/0069471 | A1 | 3/2021 | Howell |
| 2021/0085927 | A1 | 3/2021 | Howell |
| 2021/0106351 | A1 | 4/2021 | Hossack et al. |
| 2021/0113809 | A1 | 4/2021 | Howell |
| 2021/0113810 | A1 | 4/2021 | Howell |
| 2021/0121661 | A1 | 4/2021 | Howell |
| 2021/0212722 | A1 | 7/2021 | Kiev et al. |
| 2022/0087708 | A1 | 3/2022 | Chen et al. |
| 2022/0152368 | A1 | 5/2022 | Thornley et al. |
| 2022/0176081 | A1 | 6/2022 | Spataro et al. |
| 2023/0141739 | A1 | 5/2023 | Doctor et al. |
| 2023/0233227 | A1 | 7/2023 | Lindekugel et al. |
| 2023/0241353 | A1 | 8/2023 | Howell et al. |
| 2023/0241354 | A1 | 8/2023 | Howell |
| 2023/0255661 | A1 | 8/2023 | Howell |
| 2023/0277212 | A1 | 9/2023 | Howell |
| 2023/0277813 | A1 | 9/2023 | Howell |
| 2023/0277814 | A1 | 9/2023 | Howell |
| 2025/0381370 | A1 | 12/2025 | Spataro et al. |

FOREIGN PATENT DOCUMENTS

| | | | |
|---|---|---|---|
| CN | 111481303 | A | 8/2020 |
| CN | 112155683 | A | 1/2021 |
| DE | 10100332 | A1 | 7/2002 |
| DE | 202004012605 | U1 | 10/2004 |
| WO | 9108709 | A1 | 6/1991 |
| WO | 9412091 | A1 | 6/1994 |
| WO | 02087666 | A2 | 11/2002 |
| WO | 03022129 | A2 | 3/2003 |
| WO | 2011024013 | A1 | 3/2011 |
| WO | 2011057282 | A2 | 5/2011 |
| WO | 2012087506 | A2 | 6/2012 |
| WO | 2016176065 | A1 | 11/2016 |
| WO | 2017006323 | A1 | 1/2017 |
| WO | 2020076691 | A1 | 4/2020 |
| WO | 2022104149 | A1 | 5/2022 |
| WO | 2022120201 | A1 | 6/2022 |
| WO | 2023081465 | A1 | 5/2023 |
| WO | 2023122313 | A1 | 6/2023 |
| WO | 2023141170 | A1 | 7/2023 |
| WO | 2023150263 | A1 | 8/2023 |
| WO | 2023150314 | A1 | 8/2023 |
| WO | 2023158643 | A1 | 8/2023 |
| WO | 2023158645 | A1 | 8/2023 |
| WO | 2023167943 | A1 | 9/2023 |
| WO | 2023168005 | A1 | 9/2023 |
| WO | 2023168097 | A1 | 9/2023 |

OTHER PUBLICATIONS

PCT/US2021/061857 filed Dec. 3, 2021 International Search Report and Written Opinion dated Apr. 11, 2022.

Rauchwerger, Jacob Jeffrey, Michael Serle, and Jeffrey C. Astbury. "Novel Wire-Guided Scalpel to Facilitate Central Venous Catheter Insertion without a Skin Bridge." Vascular Specialist International 37 (2021).

U.S. Appl. No. 17/542,096, filed Dec. 3, 2021 Restriction Requirement dated Mar. 1, 2023.

U.S. Appl. No. 17/525,774, filed Nov. 12, 2021 Non-Final Office Action dated Jan. 24, 2024.

U.S. Appl. No. 17/542,096, filed Dec. 3, 2021 Advisory Action dated Nov. 29, 2023.

U.S. Appl. No. 17/542,096, filed Dec. 3, 2021 Final Office Action dated Sep. 20, 2023.

U.S. Appl. No. 17/542,096, filed Dec. 3, 2021 Non-Final Office Action dated Jan. 18, 2024.

U.S. Appl. No. 17/525,774, filed Nov. 12, 2021 Notice of Allowance dated Jul. 18, 2025.

U.S. Appl. No. 17/982,119, filed Nov. 7, 2022 Non-Final Office Action dated Aug. 13, 2025.

U.S. Appl. No. 18/087,699, filed Dec. 22, 2022 Non-Final Office Action dated Sep. 10, 2025.

U.S. Appl. No. 18/098,607, filed Jan. 18, 2023 Final Office Action dated Aug. 11, 2025.

U.S. Appl. No. 18/116,748, filed Mar. 2, 2023 Non-Final Office Action dated May 21, 2025.

PCT/US2022/049134 filed Nov. 7, 2022 International Search Report and Written Opinion dated Mar. 30, 2023.

PCT/US2022/053889 filed Dec. 22, 2022 International Search Report and Written Opinion dated Apr. 20, 2023.

PCT/US2023/011067 filed Jan. 18, 2023 International Search Report and Written Opinion dated May 11, 2023.

PCT/US2023/014298 filed Mar. 1, 2023 International Search Report and Written Opinion dated Jun. 1, 2023.

U.S. Appl. No. 17/542,096, filed Dec. 3, 2021 Non Final Office Action dated Jun. 1, 2023.

U.S. Appl. No. 17/525,774, filed Nov. 12, 2021 Non-Final Office Action dated Jan. 28, 2025.

U.S. Appl. No. 17/542,096, filed Dec. 3, 2021 Non-Final Office Action dated Dec. 27, 2024.

U.S. Appl. No. 17/542,096, filed Dec. 3, 2021 Notice of Allowance dated May 9, 2025.

U.S. Appl. No. 17/982,119 filed Nov. 7, 2022 Restriction Requirement dated May 5, 2025.

U.S. Appl. No. 18/098,607, filed Jan. 18, 2023 Non-Final Office Action dated Feb. 6, 2025.

U.S. Appl. No. 17/525,774, filed Nov. 12, 2021 Advisory Action dated Aug. 26, 2024.

(56) References Cited

OTHER PUBLICATIONS

U.S. Appl. No. 17/525,774, filed Nov. 12, 2021 Final Office Action dated Jun. 18, 2024.
U.S. Appl. No. 17/542,096, filed Dec. 3, 2021 Final Office Action dated Aug. 1, 2024.
PCT/US2023/012270 filed Feb. 3, 2023 International Search Report and Written Opinion dated Jun. 21, 2023.
PCT/US2023/012345 filed Feb. 3, 2023 International Search Report and Written Opinion dated Jun. 27, 2023.
PCT/US2023/013056 filed Feb. 14, 2023 International Search Report and Written Opinion dated Jun. 12, 2023.
PCT/US2023/013058 filed Jun. 7, 2023 International Search Report and Written Opinion dated Jun. 7, 2023.
PCT/US2023/014384 filed Mar. 2, 2023 International Search Report and Written Opinion dated Jun. 16, 2023.
PCT/US2023/014532 filed Mar. 3, 2023 International Search Report and Written Opinion dated Jul. 10, 2023.
U.S. Appl. No. 18/105,357, filed Feb. 3, 2023 Non-Final Office Action dated Oct. 2, 2025.
U.S. Appl. No. 18/105,743, filed Feb. 3, 2023 Non-Final Office Action dated Oct. 2, 2025.
U.S. Appl. No. 18/116,748, filed Mar. 2, 2023 Final Office Action dated Nov. 26, 2025.
U.S. Appl. No. 18/117,334, filed Mar. 3, 2023 Restriction Requirement dated Oct. 30, 2025.
U.S. Appl. No. 17/982,119, filed Nov. 7, 2022 Notice of Allowance dated Feb. 27, 2026.
U.S. Appl. No. 18/087,699, filed Dec. 22, 2022 Final Office Action dated Feb. 13, 2026.
U.S. Appl. No. 18/105,357, filed Feb. 3, 2023 Final Office Action dated Feb. 13, 2026.
U.S. Appl. No. 18/116,249, filed Mar. 1, 2023 Restriction Requirement dated Feb. 5, 2026.
U.S. Appl. No. 18/116,748, filed Mar. 2, 2023 Notice of Allowance dated Feb. 26, 2026.
U.S. Appl. No. 18/117,334, filed Mar. 3, 2023 Non-Final Office Action dated Mar. 26, 2026.

DISTAL

PROXIMAL

TRANSVERSE

LONGITUDINAL

LATERAL

PROXIMAL

DISTAL

PROXIMAL

DISTAL

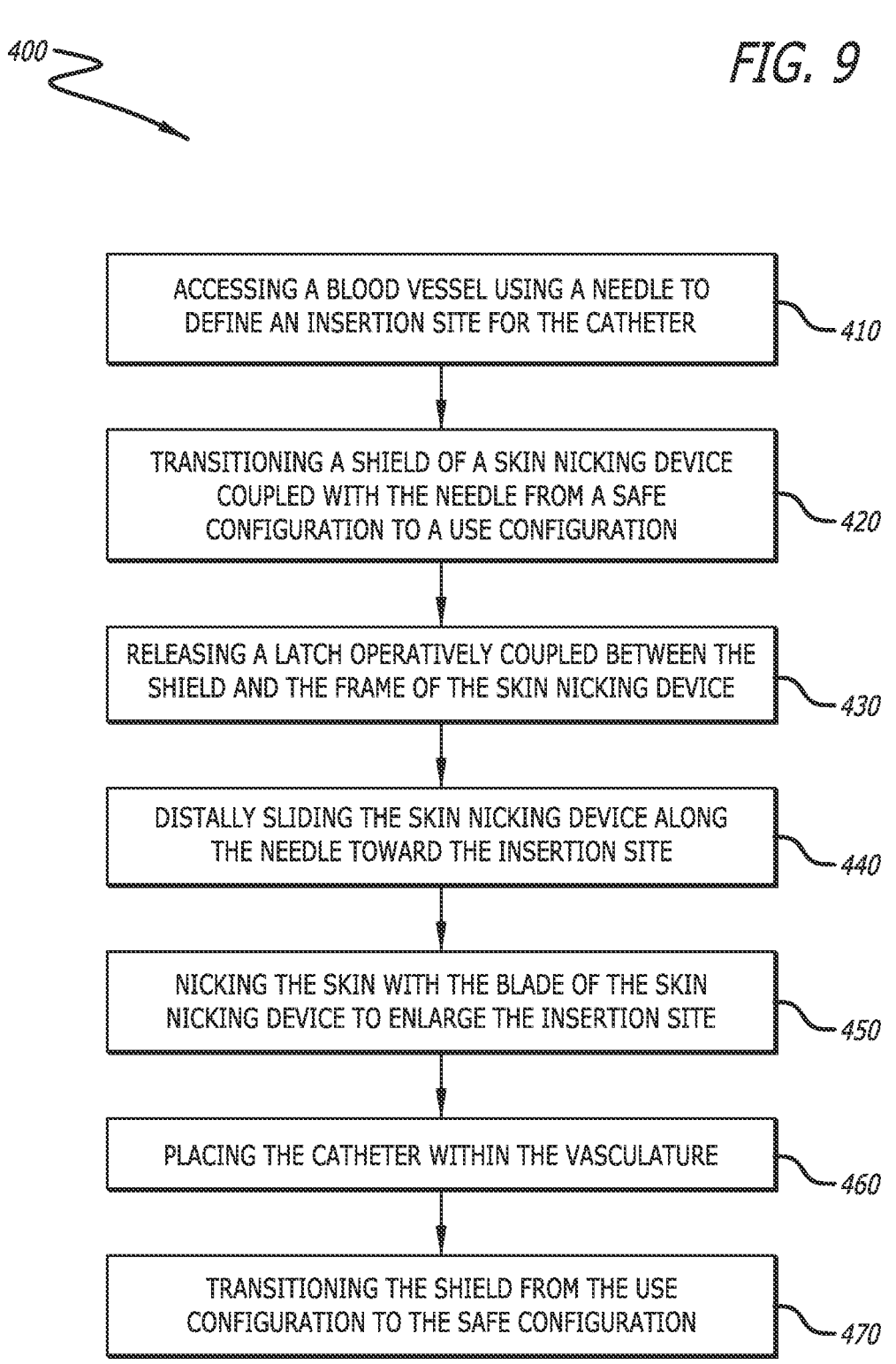

ACCESSING A BLOOD VESSEL USING A NEEDLE TO DEFINE AN INSERTION SITE FOR THE CATHETER ~410

TRANSITIONING A SHIELD OF A SKIN NICKING DEVICE COUPLED WITH THE NEEDLE FROM A SAFE CONFIGURATION TO A USE CONFIGURATION ~420

RELEASING A LATCH OPERATIVELY COUPLED BETWEEN THE SHIELD AND THE FRAME OF THE SKIN NICKING DEVICE ~430

DISTALLY SLIDING THE SKIN NICKING DEVICE ALONG THE NEEDLE TOWARD THE INSERTION SITE ~440

NICKING THE SKIN WITH THE BLADE OF THE SKIN NICKING DEVICE TO ENLARGE THE INSERTION SITE ~450

PLACING THE CATHETER WITHIN THE VASCULATURE ~460

TRANSITIONING THE SHIELD FROM THE USE CONFIGURATION TO THE SAFE CONFIGURATION ~470

SKIN NICKING DEVICE FOR CATHETER PLACEMENT SYSTEM

PRIORITY

This application claims the benefit of priority to U.S. Provisional Application No. 63/310,531, filed Feb. 15, 2022, which is incorporated by reference in its entirety into this application.

BACKGROUND

Central venous catheter ("CVCs") are commonly introduced into patients and advanced along a vasculature by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma or increased risk of infection. There is a relatively high potential for touch contamination due to the number of medical devices that need to be interchanged during the Seldinger technique. As such, advanced catheter placement systems have been developed to reduce the number of steps and medical devices involved in placing a catheter, such as a CVC, into a patient.

Some of these advanced catheter placement systems include accessing a vasculature with a needle and stabilizing the access site with a guidewire. Once the guidewire is placed, a scalpel may be used to cut or nick the skin and fascia at the insertion site to ease the insertion of the catheter. If the skin nick is not created properly, a skin bridge may form, impeding insertion of the catheter through the skin into the vessel. A skin nicking device may be used to create a repeatable depth of cut, reducing the likelihood of leaving skin bridges around the insertion site. Disclosed herein are advanced catheter placement systems and associated methods for nicking the skin at the insertion site to eliminate skin bridges impeding the insertion of the catheter into the vasculature.

SUMMARY

Disclosed herein is a catheter placement device that, according to some embodiments, includes a needle configured to establish an insertion site for a vascular catheter, where the needle defines a needle lumen extending between a distal end and a needle hub at a proximal end. The catheter placement device further includes a skin nicking device slidably coupled with the needle, where the skin nicking device includes a blade configured to nick a skin adjacent the insertion site to enlarge the insertion site and a shield, and where the shield is transitionable between (i) a safe configuration, where the blade is encapsulated by the shield, and (ii) a use configuration, where the blade is exposed for use in nicking the skin.

In some embodiments, the skin nicking device includes a frame coupled with the blade and the shield. In some embodiments, the frame is coupled with the needle hub such that the frame is positionally retained by the needle hub in the absence of a separating force applied to the skin nicking device by a clinician.

In some embodiments, the shield is rotatably coupled with the frame such that the shield is rotatable between the safe configuration and the use configuration. In some embodiments, the shield is slidably coupled with the frame such that the shield is displaceable between the safe configuration and the use configuration. In some embodiments, the shield is longitudinally displaceable between a distal position corresponding to the safe configuration and a proximal position corresponding to the use configuration. In some embodiments, the shield is biased toward the safe configuration.

In some embodiments, the skin nicking device further includes a latch operatively coupled between the shield and frame, and the latch is configured to prevent the shield from transitioning away from the safe configuration toward the use configuration in the absence of a deliberate action by the clinician. In some embodiments, the latch includes an actuator configured to release the latch as a result of the deliberate action, thereby allowing the shield to transition away from the safe configuration toward the use configuration.

In some embodiments, the blade is fixedly attached to the frame such that the blade extends distally away from the frame. In some embodiments, the blade includes a sharp edge and a dull edge, where the sharp edge faces away from the dull edge, and where sharp edge is disposed at an angle with respect to the dull edge. In some embodiments, the sharp edge and the dull edge converge to define a sharp tip at a distal end of the blade.

In some embodiments, the blade is fixedly attached to the frame such that (i) the dull edge faces the needle, (ii) the sharp edge faces radially away from the needle, and (iii) the sharp tip is disposed immediately adjacent the needle.

In some embodiments, the skin nicking device includes a tubular sheath coupled with the frame so that the tubular sheath extends distally away from the frame along the needle, and the needle is disposed within a lumen of the tubular sheath. In some embodiments, the sharp tip is disposed radially inward of an outside diameter surface of the tubular sheath. In some embodiments, the sharp tip is embedded within a wall of the tubular sheath.

In some embodiments, the skin nicking device includes a second blade fixedly coupled with the frame such that the second blade is disposed opposite the blade. In some embodiments, the shield is configured to encapsulate the second blade in the safe configuration and expose the second blade in the use configuration.

Also disclosed herein is a method of placing a catheter within a patient vasculature that, according to some embodiments, includes (i) accessing a blood vessel using a needle to define an insertion site for the catheter, (ii) transitioning a shield of a skin nicking device coupled with the needle from a safe configuration to a use configuration to expose a blade of the skin nicking device, (iii) distally sliding the skin nicking device along the needle toward the insertion site, (iv) nicking the skin with the blade to enlarge the insertion site, and (v) placing the catheter within the vasculature.

In some embodiments of the method, nicking the skin includes distally sliding the skin nicking device along the needle so that the blade extends into the insertion site.

In some embodiments, the method further includes decoupling a frame of the skin nicking device from a needle hub of the needle.

In some embodiments, the method further includes releasing a latch operatively coupled between the shield and the frame to enable the shield to transition from the safe configuration to the use configuration.

In some embodiments, the method further includes transitioning the shield from the use configuration to the safe configuration to encapsulate the blade.

In some embodiments of the method, transitioning the shield includes rotating the shield.

In some embodiments of the method, transitioning the shield from the safe configuration to the use configuration includes slidably displacing the shield from a distal position to a proximal position.

In some embodiments of the method, transitioning the shield from the safe configuration to the use configuration includes contacting the skin with the shield and further distally displacing the skin nicking device along the needle so that the skin applies a proximally oriented force to the shield to displace the shield from the distal position toward the proximal position.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 9 illustrates a flow chart of an exemplary method of placing a catheter using a catheter placement system, in accordance with some embodiments.

DESCRIPTION

Figure 1A:
FIG. 1A shows a perspective view of a catheter placement system in an unfolded configuration, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method. Additionally, all embodiments disclosed herein are combinable and/or interchangeable unless stated otherwise or such combination or interchange would be contrary to the stated operability of either embodiment.

The phrases "connected to," "coupled to/with," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

Unless defined otherwise, all technical and scientific terms used herein have the same meaning as commonly understood by those of ordinary skill in the art.

Figure 1B:
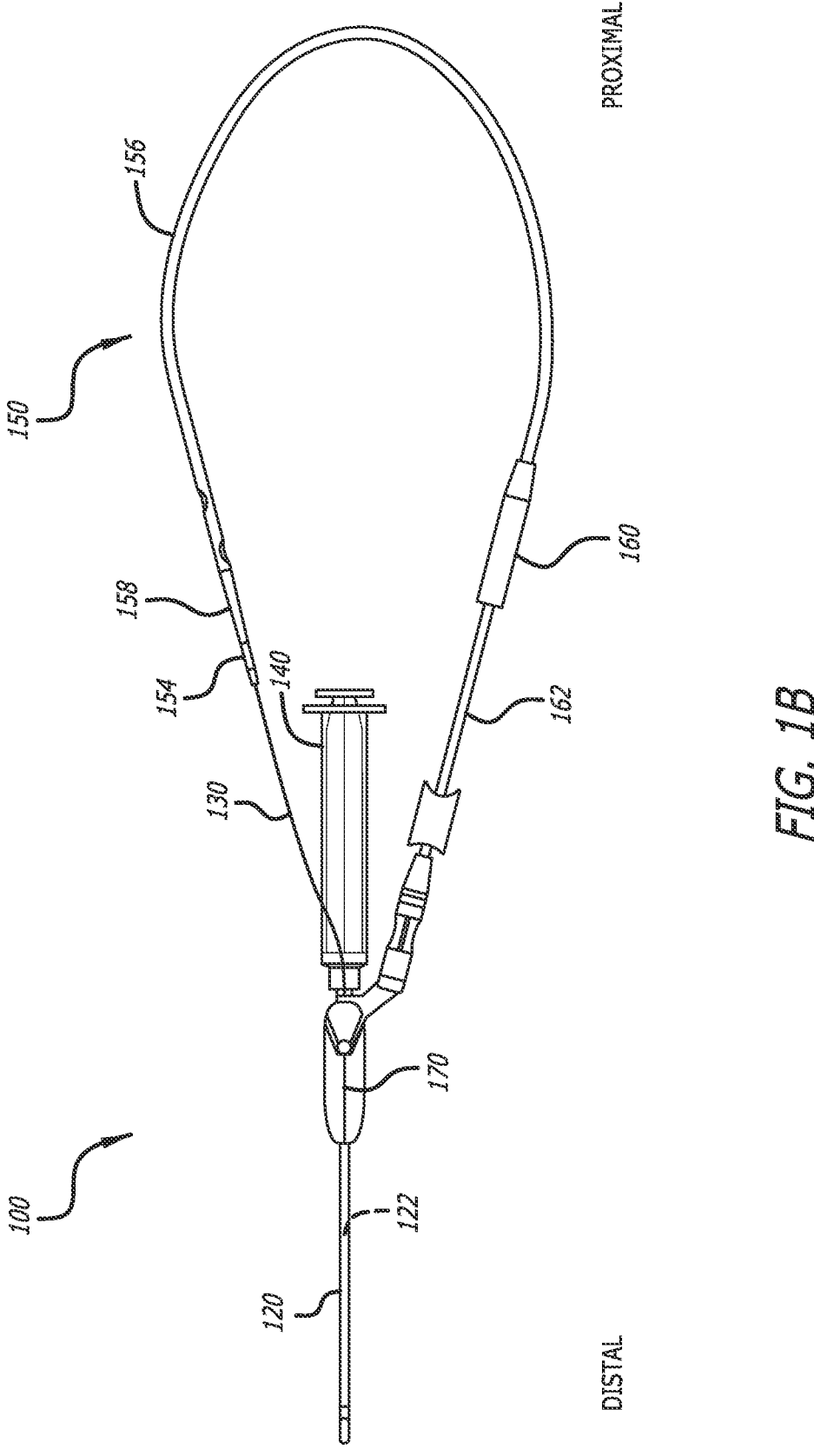
FIG. 1B shows a plan view of a catheter placement system in a folded configuration ready for use, in accordance with embodiments disclosed herein.
Figure 1C:
FIG. 1C shows a perspective view of a catheter placement system in a folded configuration, in accordance with embodiments disclosed herein.

FIGS. 1A-1C show an exemplary advanced catheter placement system ("system") 100, generally including a needle 120, a guidewire 130, a syringe system 140, a catheter 150, and a needle housing ("housing") 170. FIG. 1A shows the system 100 in an unfolded configuration for ease of illustration. FIG. 1B shows a plan view of the system 100 in a folded configuration ready for use. FIG. 1C shows a perspective view the system 100 in a folded configuration. In an embodiment the catheter placement system 100 can be a Rapidly Insertable Central Catheter (RICC) placement system 100 configured to place a RICC 150. However, it will be appreciated that other catheter placement systems configured to place other types of catheters are also contemplated. Exemplary catheters 150 can also include peripheral intravenous (PIV) catheters, peripherally inserted central catheter (PICC), central venous catheters (CVC), midline catheters, dialysis catheters, single lumen catheters, multi-lumen catheters, or the like.

In an embodiment, the catheter 150 can generally include a catheter body 152 supported at a proximal end by a catheter hub ("hub") 160. The hub 160 can include one or more extension legs 162 extending proximally therefrom. Each extension leg of the one or more extension legs 162 can be in fluid communication with a lumen of the catheter body 152. The catheter body 152 can include a first section 154 disposed distally, a second section 156 disposed proximally, and a transition section 158 disposed therebetween. The first section 154 can define a single lumen and have a first outer diameter, the second section 156 can define two or more lumen and can have a second diameter larger than the first diameter. The transition section 158 disposed between the first section 154 and the second section 156 can define a tapered shape extending from the first diameter of the first section to the second diameter of the second section. A guidewire 130 can extend through a lumen of the catheter 150 from a proximal end of an extension leg 162, to a distal tip of the first section 154.

Figure 2:
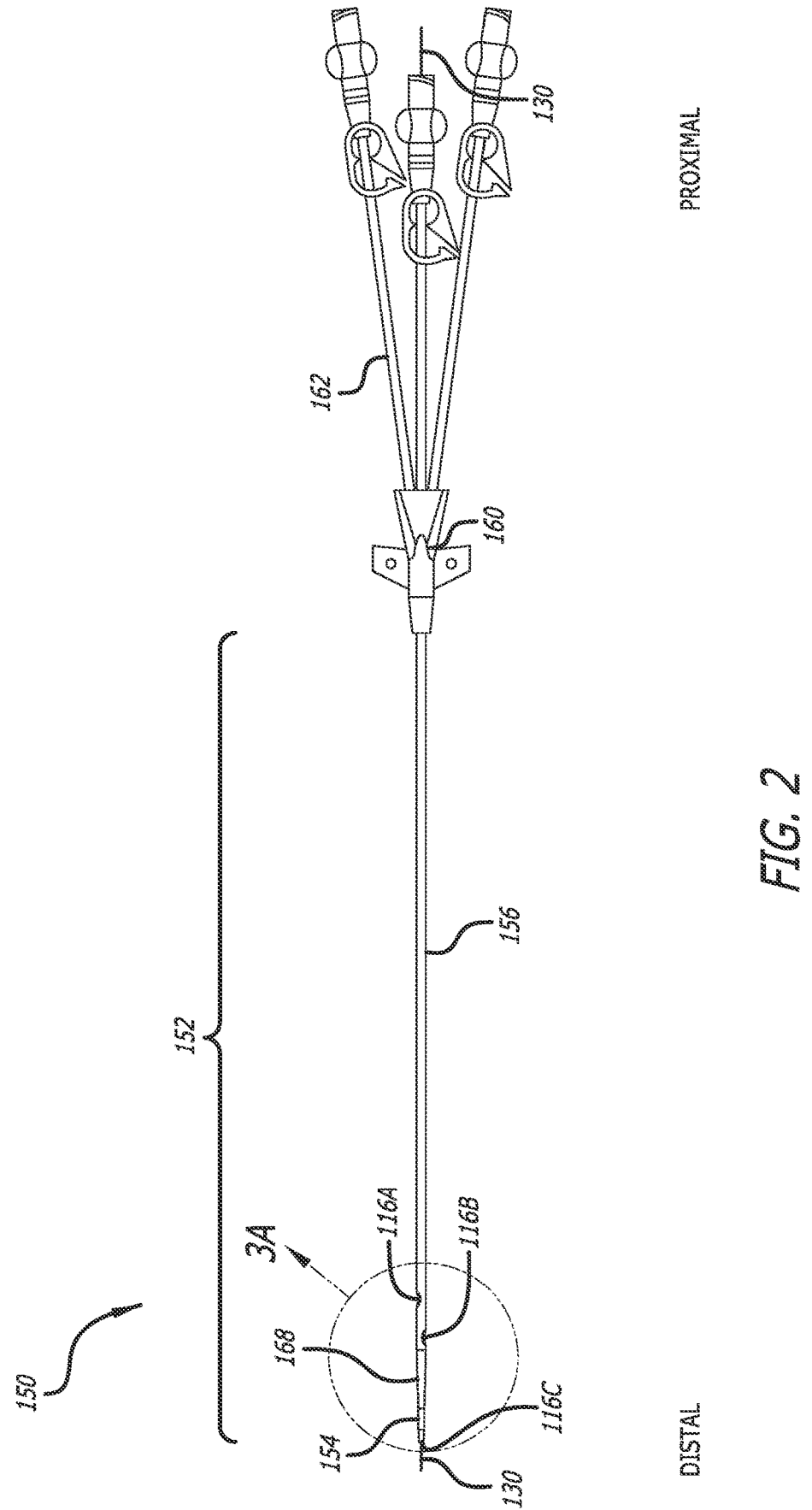
FIG. 2 shows a side view of a catheter of a catheter placement system in an unfolded configuration, in accordance with embodiments disclosed herein.

FIG. 2 shows further details of an exemplary catheter 150 of the system 100. As described herein, different sections of the catheter 150 are required to perform different functions and as such are required to display different mechanical properties. For example, the first section 154 and the transition section 158 can provide a more rigid mechanical properties or harder durometer material relative to the second section 156. As such, the first section 154 and transition section 158 can withstand greater axial forces without kinking or collapsing, as theses sections are urged distally, forming and dilating the insertion site. The second section 156 can be formed of a softer durometer, or a more compliant material to facilitate negotiating the second section 156 through tortuous vascular pathways.

Figures 3A, 3B, 3C:
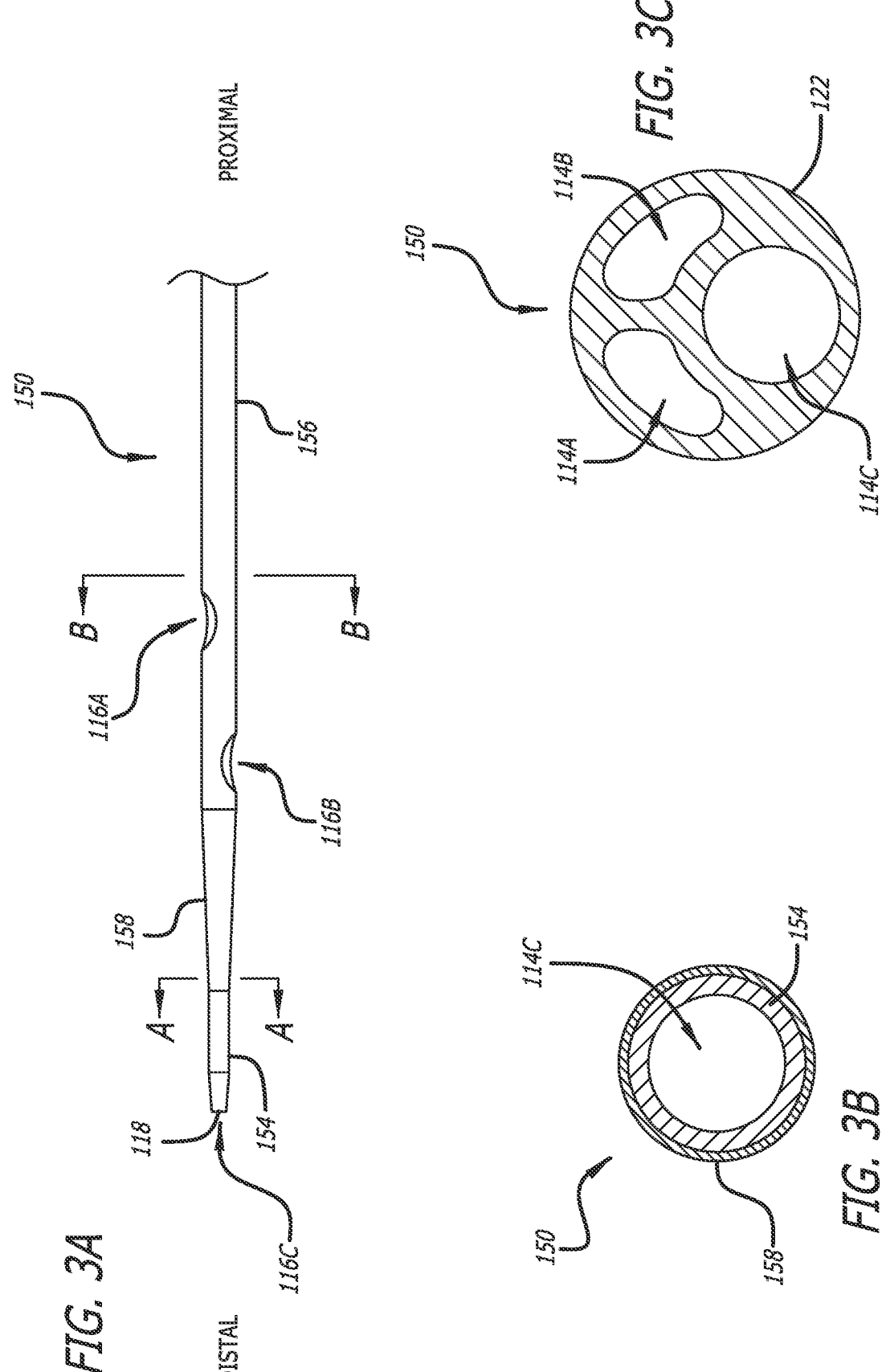
FIG. 3A shows close up detail of a distal portion of the catheter of FIG. 2, in accordance with embodiments disclosed herein.
FIGS. 3B-3C show cross-section views of the catheter of FIG. 3A, in accordance with embodiments disclosed herein.

FIGS. 3A-3C show further details of a distal portion of the catheter 150, including the first section 154, the second section 156, and the transition section 158. In an embodiment, the second section 156 can include a proximal lumen 114A terminating at a proximal lumen aperture 116A, and a medial lumen 114B terminating at a medial lumen aperture 116B. Each of the proximal lumen aperture 116A and the medial lumen aperture 116B can extend through a side wall of the second section 156. Each of the proximal lumen aperture 116A and the medial lumen aperture 116B can be disposed proximally of the transition section 158. The proximal lumen aperture 116A can be disposed proximally of the medial lumen aperture 116B.

FIG. 3B shows a cross section view of the catheter body 152 at point "A" of FIG. 3A. As shown, the first section 154 can define a single lumen and a relatively smaller outer diameter. In an embodiment, a proximal portion of the first section 154 can be received within a distal portion of the transition section 158. A distal lumen 114C of the catheter 150 can extend to a distal tip 118 of the catheter 150 and can communicate with a distal lumen aperture 116C. FIG. 3C shows a cross section view of the second section 156 at point "B" of FIG. 3A, showing the proximal lumen 114A, medial lumen 114B and distal lumen 114C.

Figure 4:
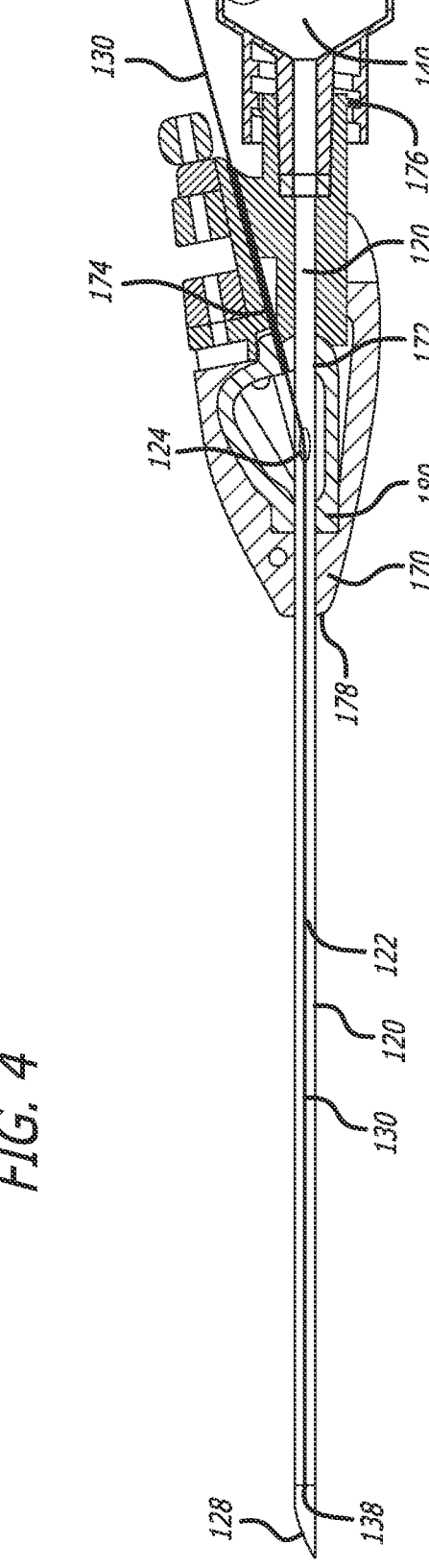
FIG. 4 shows a longitudinal cross-section view of a distal portion of a catheter placement system, in accordance with embodiments disclosed herein.

FIG. 4 shows a longitudinal cross-section view of a distal portion of a catheter placement system 100 including the needle 120, guidewire 130, a distal portion of the syringe system 140, and needle housing ("housing") 170 including a needle splitter system 180, as described in more detail herein. In an embodiment, a proximal end of the needle 120 can be supported by a needle hub which can be coupled to, and supported by, a distal end of the syringe system 140. The syringe system 140 can be in fluid communication with needle lumen 122. The syringe system 140 can be configured to form a vacuum therein and draw a fluid flow proximally through the needle lumen 122. In an embodiment, the needle 120 can include a guidewire aperture 124 disposed in a wall of the needle 120 and communicating with a needle lumen 122. A distal portion of the guidewire 130 can extend through the guidewire aperture 124 and into the needle lumen 122. In an embodiment, a distal tip 138 of the guidewire 130 can be disposed proximate a distal tip 128 of the needle 120. As such, once the needle 120 accesses the vasculature, the distal tip 138 of the guidewire 130 can be positioned within the vasculature, expediting the placement of the catheter 150.

In an embodiment, the catheter placement system 100 can include a housing 170. The housing 170 can include a housing lumen 172 extending between a proximal end 176 and a distal end 178 of the housing 170. The housing 170 can further include a guidewire lumen 174 communicating with the housing lumen 172 and extending at an angle therefrom. A portion of the needle 120 can slidably engage the housing lumen 172. Further, the proximal end 176 of the housing can releasably engage one or both of a needle hub and a distal portion of the syringe system 140. When the housing 170 is engaged with the syringe system 140 the guidewire aperture 124 of the needle 120 can align with the guidewire lumen 174 of the housing 170. As such, the guidewire 130 can extend through the guidewire lumen 174 of the housing 170, through the guidewire aperture 124 of the needle 120 and into the needle lumen 122.

Figure 5A:
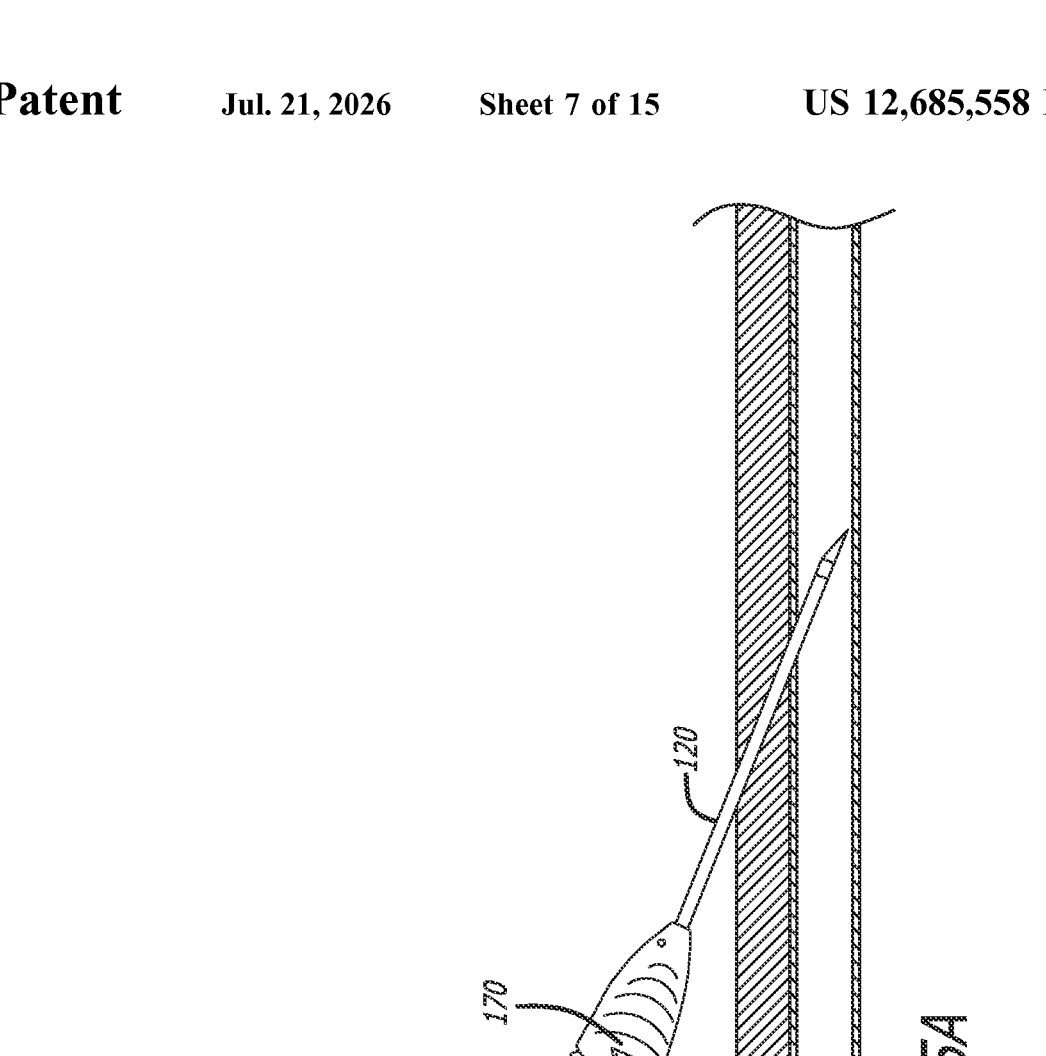
FIGS. 5A-5E show an exemplary method of use for a catheter placement system, in accordance with embodiments disclosed herein.
Figure 5B:
Figure 5C:

FIGS. 5A-5E show an exemplary method of placing a catheter 150 using the catheter placement system 100. As shown in FIG. 5A, the needle 120 can penetrate surface tissues 90 of the patient and access a vasculature 80, forming an insertion site. As shown in FIG. 5B, a syringe system 140, or similar device can form a vacuum and draw a fluid flow proximally through a needle lumen 122. A user can observe a color or pulsatile flow and confirm correct vascular access. Where incorrect vascular access is confirmed, the needle 120 can be withdrawn and the insertion site can be closed. As shown in FIG. 5C, once correct vascular access has been confirmed, the guidewire 130 can then be advanced through the needle lumen 122 and into the vasculature 80 to maintain patency of the insertion site.

Figure 5D:
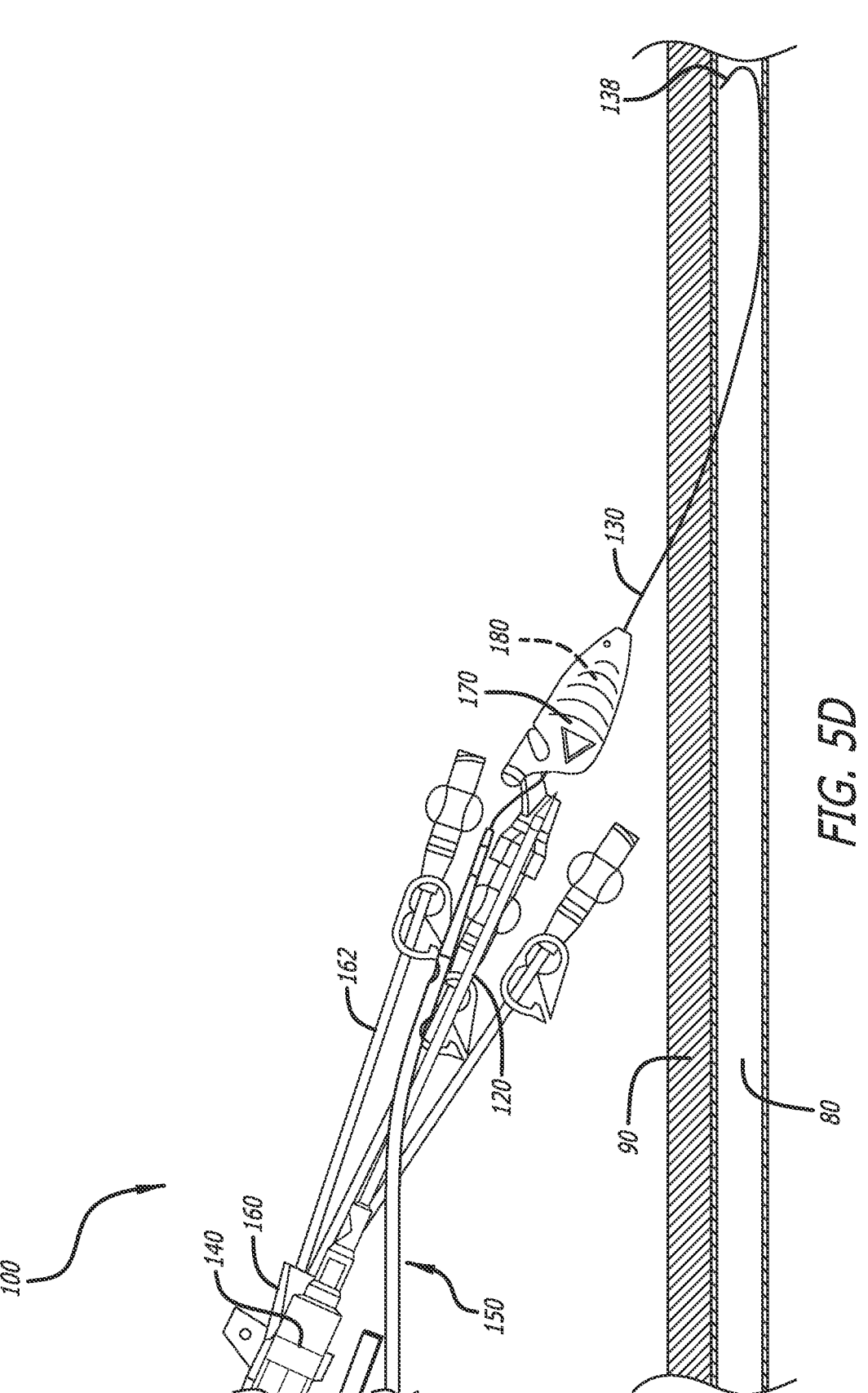

As shown in FIG. 5D, the needle 120 and syringe system 140 assembly can be withdrawn proximally to disengage the needle 120 from the guidewire 130 while leaving a distal portion of the guidewire 130 in place within the vasculature 80. As described in more detail herein, the housing 170 can include a splitter system 180 configured to split the needle 120 longitudinally, as the needle 120 is withdrawn proximally. A portion of the guidewire 130 can pass between the two halves of the needle 120 to allow the needle 120 to disengage the guidewire 130.

Figure 5E:
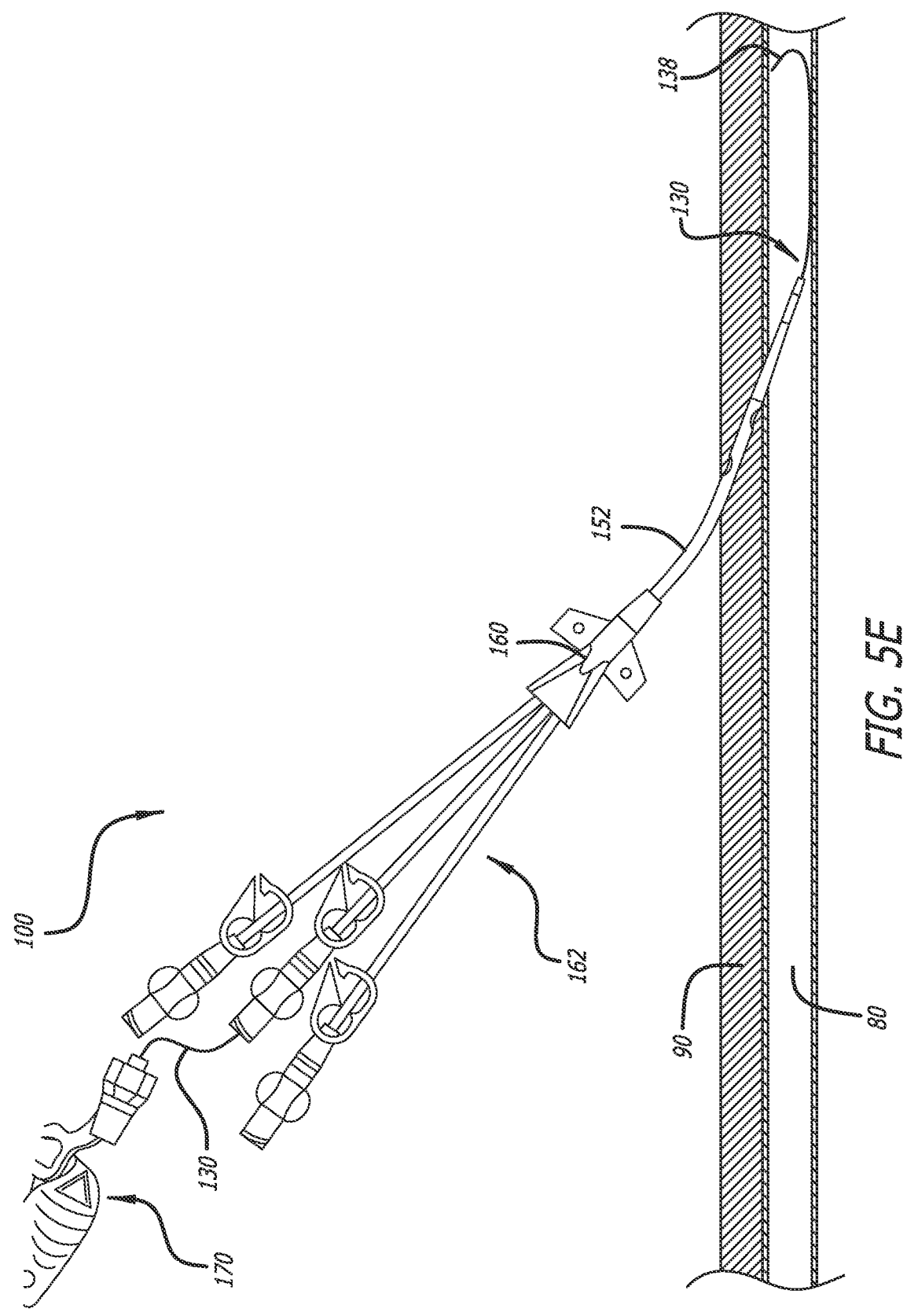

As shown in FIG. 5E, with the needle 120 and syringe system 140 assembly disengaged from the guidewire 130, the catheter 150 can then be advanced over the guidewire 130 and into the vasculature. The first section 154 of the catheter 150, having only a single lumen and defining a relatively smaller outer diameter, can enter the vasculature 80 over the guidewire 130, anchoring the insertion site. The transition section 158 can then be urged distally, dilating the insertion site to allow the relatively larger diameter second section 156, defining two or more lumen, to enter the vasculature 80. Once the catheter 150 has been placed, the guidewire 130 can be withdrawn proximally.

Further details and embodiments of such catheter placement systems 100 can be found, for example, in U.S. Pat. No. 10,376,675, US 2019/0255294, US 2021/0069471, US 2021/0085927, US 2021/0113809, US 2021/0113810, US 2021/0121661, US 2021/0121667, US 2021/0228843, US 2021/0322729, US 2021/0330941, US 2021/0330942, US 2021/0361915, US 2021/0402153, US 2021/0402149, US 2022/0001138, U.S. patent application Ser. No. 17/390,682 filed Jul. 30, 2021, and U.S. Provisional Patent Application No. 63/229,862 filed Aug. 5, 2021, each of which is incorporated by reference in its entirety into this application.

Figures 6A, 6B:
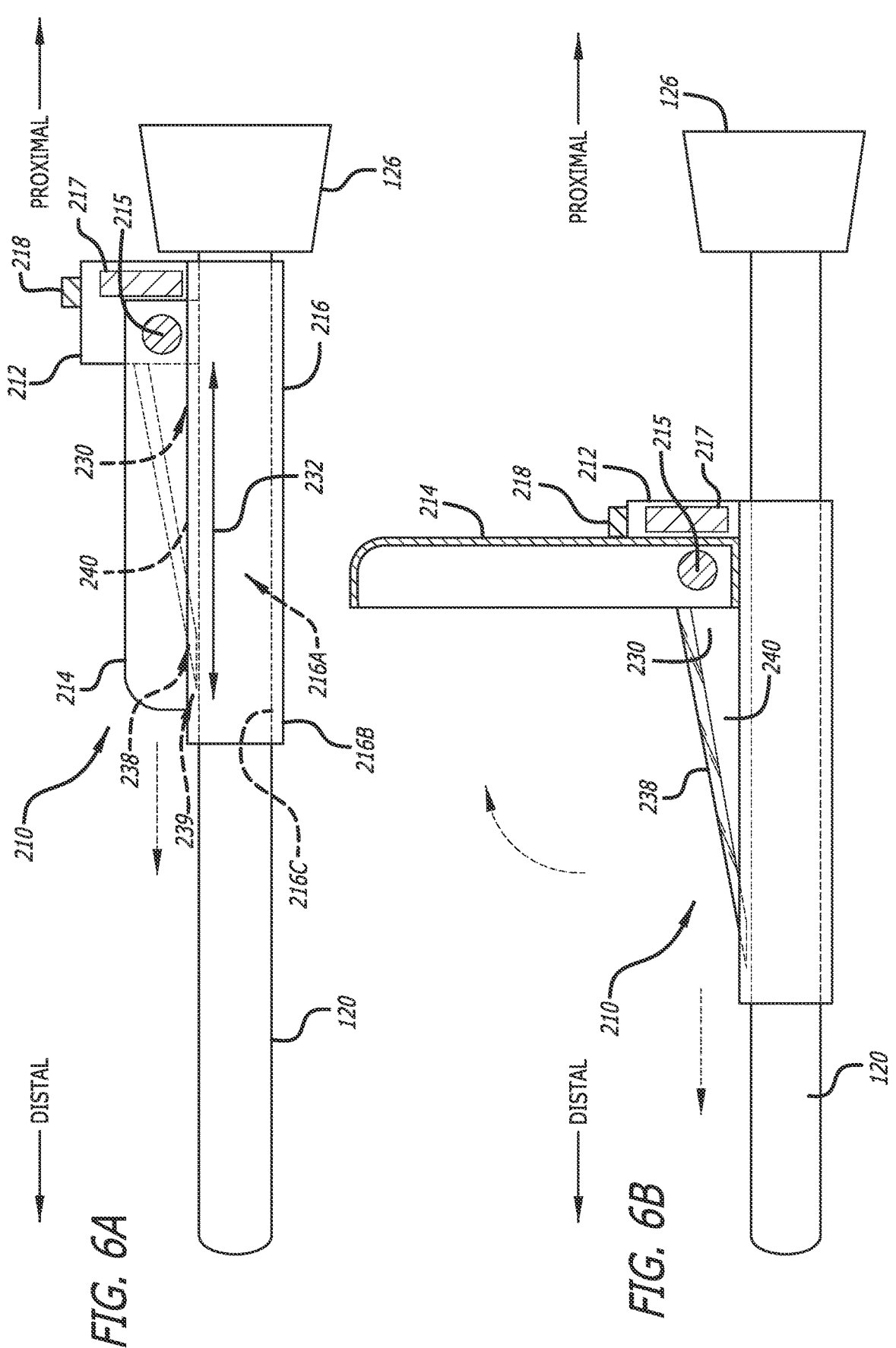
FIG. 6A shows a cross-sectional view of a skin nicking device in a safe configuration, in accordance with some embodiments.
FIG. 6B illustrates a cross-sectional view of the skin nicking device in a use configuration, in accordance with some embodiments.

FIG. 6A illustrates a side view of a skin nicking device 210 having a shield 214 disposed in a safe configuration, in accordance with some embodiments. In some embodiments, the skin nicking device 210 may be used in concert with the catheter placement system 100. In some embodiments, the skin nicking device 210 may be integrated into the catheter placement system 100 to nick the skin as the catheter 150 is placed within the vasculature 80.

The skin nicking device 210 may be deployed with the needle 120 or included with the need to define a catheter placement device. The skin nicking device 210 is configured to slide along the needle 120 and in some embodiments, detachably couple with a needle hub 126. The skin nicking device 210 may be configured to slide proximally and/or distally along the needle 120. The skin nicking device 210 includes a blade 230 that is generally configured to nick/cut skin adjacent a catheter insertion site so as to enlarge the insertion site. In some embodiments, the skin nicking device 210 may include more than one blade 230. The skin nicking device 210 (or more specifically, the shield 214) is configured to transition between the safe configuration (FIG. 6A) and use configuration (FIG. 6B). In the safe configuration, the blade 230 is encapsulated (or otherwise rendered inaccessible) by the shield 214. In the use configuration, the blade 230 is exposed to enable use of the blade 230 to nick the skin.

In some embodiments, the skin nicking device 210 may include a frame 212, where the shield 214 coupled to the frame 212. In some embodiments, the shield 214 may be hingedly/rotatably coupled to the frame 212 by a hinge 215. In some embodiments, the skin nicking device 210 may include blade 230 extending distally from the frame 212. In some embodiments, the shield 214 may be configured to cover the blade 230 to prevent accidental sticks in the safe configuration. The shield 214 may be configured to transition between the safe configuration and the use configuration, as will be described in more detail herein. In some embodiments, the blade 230 may have a blade length 232, a dull edge 240, and a sharp edge 238. In some embodiments, the dull edge 240 may be disposed adjacent the needle 120 such that there is substantially no gap between the dull edge 240 and the needle 120, thereby eliminating the possibility of generating a skin bridge when the blade 230 nicks the skin. In some embodiments, the skin nicking device 210 may be provided separately from the needle 120 and assembled onto the needle 120 at the point of use. In other embodiments, the skin nicking device 210 and the needle 120 may be pre-assembled (i.e., coupled together). In an embodiment, the frame 212 may be detachably couple with the needle hub 126 such that the frame 212 is positionally retained by the needle hub 126 in the absence of a separating force applied to the skin nicking device 210 by the clinician. The frame 212 may be coupled to the needle hub 126 in a snap fit, a press fit, an interference fit, a magnetic fit, or the like.

The blade 230 is fixedly attached to the frame 212 such that the blade 230 extends distally away from the frame 212. The blade includes the sharp edge 238 and a dull edge 240, where the sharp edge 238 faces away from the dull edge 240. The sharp edge 238 is disposed at an angle with respect to the dull edge 240, and the sharp edge 238 and the dull edge 240 converge to define a sharp tip 239 at a distal end of the blade 230.

In some embodiments, the skin nicking device 210 includes a tubular sheath 216 coupled with the frame 212 so that the tubular sheath 216 extends distally away from the frame 212 along the needle 120. In such embodiments, the needle 120 is disposed within a lumen 216A of the tubular sheath 216 such the needle 120 is slidable within the lumen 216A. In some embodiments, the sharp tip 239 is disposed radially inward of an outside diameter surface 216B of the tubular sheath 216. In some embodiments, the sharp tip 239 is embedded within a wall 216C of the tubular sheath 216. In some embodiments, the sheath 216 may be omitted.

FIG. 6B illustrates a side view of the skin nicking device 210 where the shield 214 is disposed in the use configuration. The shield 214 is rotated toward a perpendicular orientation with respect to the needle 120, thereby exposing the blade 230, i.e., making the blade 130 available for nicking the skin. In some embodiments, the shield 214 may be moved through any angle of the range 0-180° in relation to the needle 120. With the shield 214 disposed in the use configuration, the frame 212 including the blade 230 may be slid distally along the needle 120 so that the blade 230 is inserted into the insertion site to nick the skin. In use, the frame 212 including the blade 230 may be displaced proximally along the needle 120 away from the insertion site after the skin has been nicked. In some embodiments, the frame 212 may configured to recouple with and be retained by the needle hub 126. The shield 214 may be transitioned back from the use configuration of FIG. 6B to the safe configuration of FIG. 6A.

Referring to FIGS. 6A and 6B, in some embodiments, the skin nicking device 210 may include a latch 217 operatively coupled between the shield 214 and frame 212. The latch 217 may be configured to lock the shield 214 in the safe configuration so as to prevent the shield 214 from transitioning away from the safe configuration toward the use configuration in the absence of a deliberate action by the clinician. In some embodiments, the latch 217 includes an actuator 218 configured to release the latch 217 as a result of the deliberate action, thereby allowing the shield 214 to transition away from the safe configuration toward the use configuration.

Figure 7A:
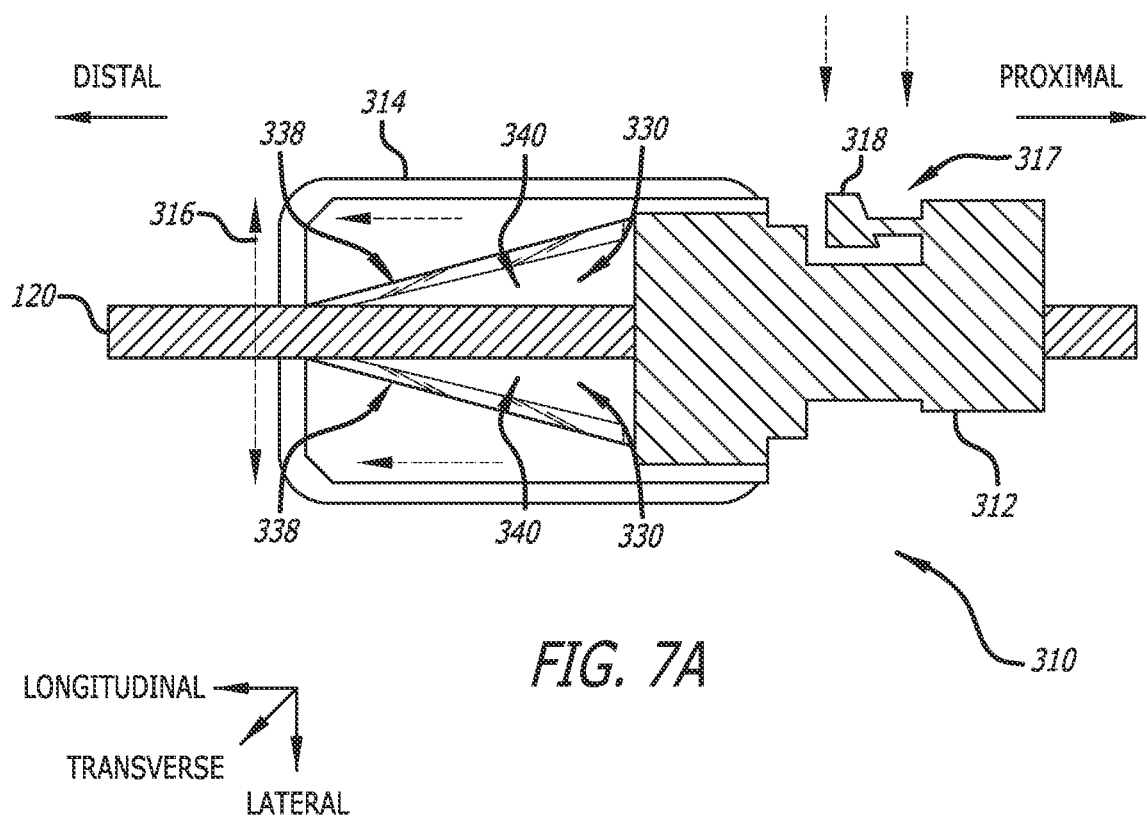
FIGS. 7A-7B illustrate a cross-sectional view of the skin nicking device including a safety, in accordance with some embodiments.
Figure 7B:
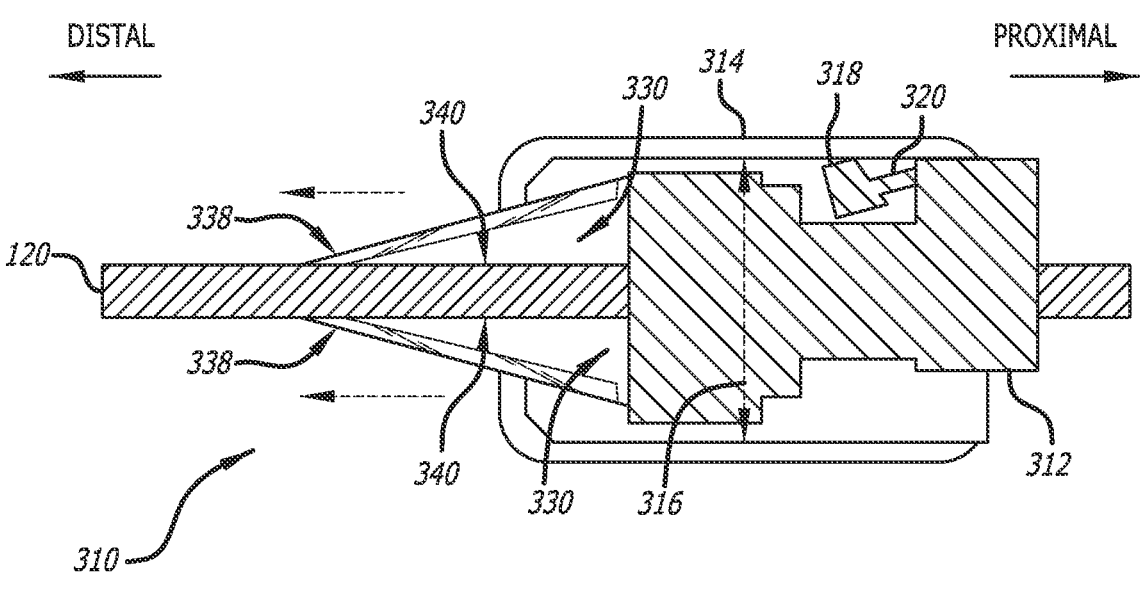

FIGS. 7A-7B illustrate another embodiment of a skin nicking device 310 that can, in certain respects, resemble components of the skin nicking device 310 described in connection with FIGS. 6A-6B. It will be appreciated that all the illustrated embodiments may have analogous features. Accordingly, like features are designated with like reference numerals, with the leading digits incremented to "3." For instance, the shield is designated as "214" in FIGS. 6A-6B, and an analogous shield is designated as "314" in FIGS. 7A-7B. Relevant disclosure set forth above regarding similarly identified features thus may not be repeated hereafter. Moreover, specific features of the skin nicking device 310 and related components shown in FIGS. 6A-6B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the skin nicking device 310 of FIGS. 7A-7B. Any suitable combination of the features, and variations of the same, described with respect to the skin nicking device 310 and components illustrated in FIGS. 6A-6B can be employed with the skin nicking device 310 and components of FIGS. 7A-7B, and vice versa.

FIGS. 7A-7B illustrate a cross-sectional views of the skin nicking device 310 transitioning between the safe configuration (FIG. 7A) and the use configuration (FIG. 7B). The skin nicking device 310 includes two blades 330 disposed opposite each other with respect to the needle 120. The skin nicking device 310 further includes a shield 314 that is displaceable (e.g., longitudinally slidable) between the safe configuration and the use configuration. The shield 314 is configured to encapsulate the blades 330 (or otherwise render the blades 330 inaccessible) in the safe configuration. In some embodiments, the blades 330 may be configured to nest within or be covered by the shield 314. The shield 314 is configured for longitudinal displacement between (i) a distal position corresponding to the safe configuration, where the blades 330 are encapsulated within the shield 314 and (ii) a proximal position corresponding to the use configuration, where the blades 330 extend distally from the shield 314 (i.e., exposed). In some embodiments, the shield 314 may be biased towards the safe configuration, e.g., spring loaded toward the safe configuration.

The skin nicking device 310 may include a latch 317 operatively coupled between the shield 314 and frame 312. The latch 317 may be configured to lock the shield 314 in the safe configuration so as to prevent the shield 314 from transitioning away from the safe configuration toward the use configuration in the absence of a deliberate action by the clinician. In some embodiments, the latch 317 includes an actuator 318 configured to release the latch 317 as a result of the deliberate action, thereby allowing the shield 314 to transition away from the safe configuration toward the use configuration. In some embodiments, the shield 314 may define shield diameter or width 316. In some embodiments, the actuator 318 of the latch 317 in a non-depressed state may extend beyond the shield diameter 316, where the latch 317 may impede proximal displacement of the shield 314, ensuring the shield 314 remains in the safe configuration. In a depressed state, the actuator 318 may be disposed within the shield diameter 316, thereby allowing proximal displacement of the shield 314 toward the use configuration.

Figures 8A, 8B:
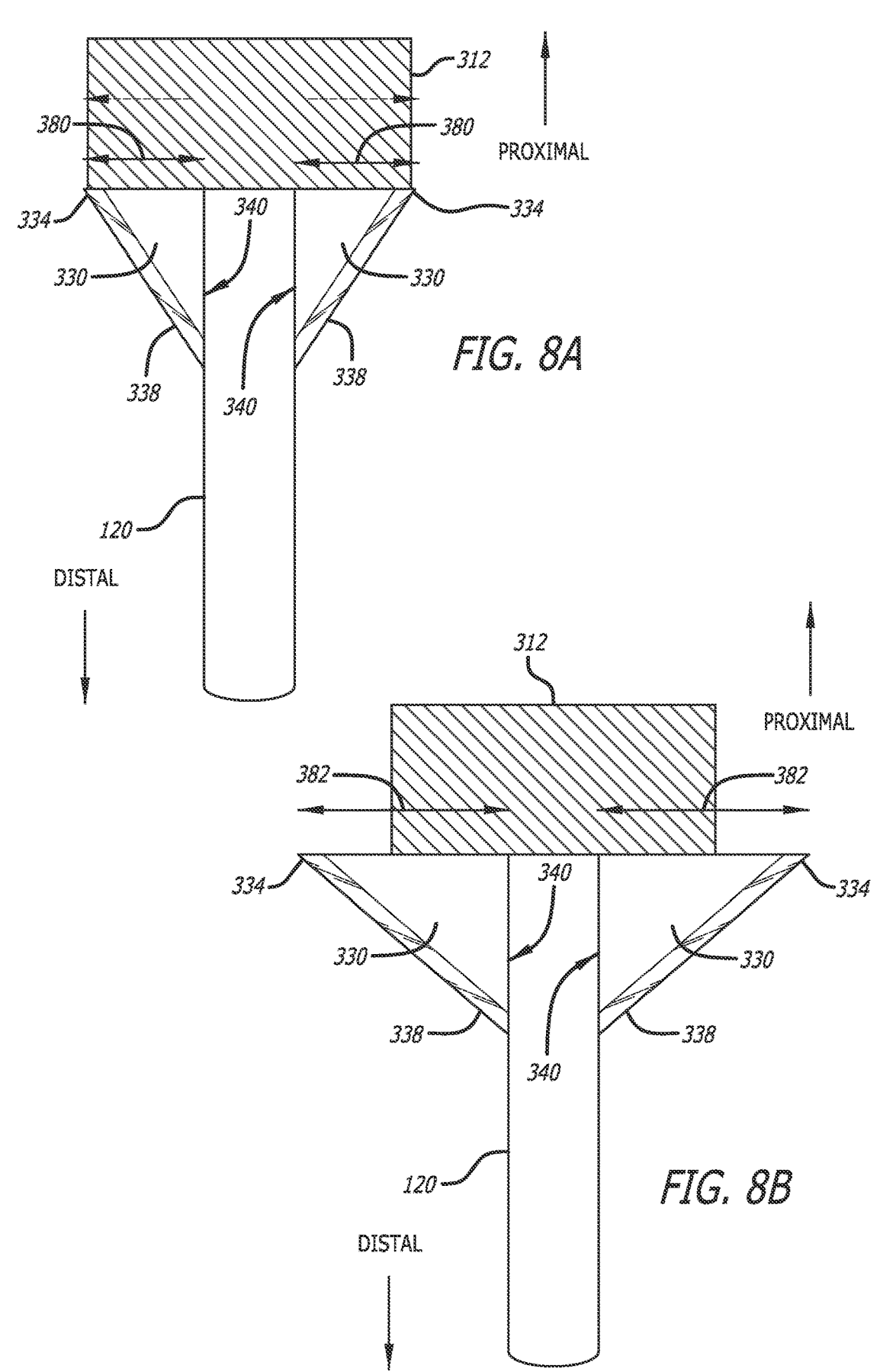
FIGS. 8A-8B illustrate a plan view of the skin nicking device, in accordance with some embodiments.

Referring to FIGS. 8A-8B, in some embodiments, the blades 330 may be moveably coupled with the frame 312 such that a proximal ends 334 of each of the blades 330 may be laterally moveable with respect to the needle 120. For example, as illustrated in FIG. 8A, each of the blades 330 may extend a first distance 380 laterally away from the needle 120. To accommodate a larger sized catheter, the proximal ends 334 of the blades 330 may be moveable so as to laterally extend further to a second distance 382 from the needle 120. The second length 382 may allow the blades 330 to generate a larger skin nick during insertion of the needle 120. In some embodiments, the blades 330 may be manually extended from the needle 120 or may be actuated to extend from the needle 120. Advantageously, extending the proximal ends 334 of the blades 330 may be configured to generate a larger skin nick during insertion of the needle 120, allowing the skin nicking device 310 to accommodate catheters of all sizes.

FIG. 9 illustrates a flow chart of an exemplary method 400 of placing a catheter within a patient vasculature that may include all or any subset of the following steps, actions, or processes. The method 400 may include accessing a blood vessel using a needle to define an insertion site for the catheter (block 410).

The method 400 may further include transitioning a shield of a skin nicking device coupled with the needle from a safe configuration to a use configuration to expose a blade of the skin nicking device (block 420). In some embodiments of the method, transitioning the shield includes rotating the shield. In some embodiments of the method, transitioning the shield from the safe configuration to the use configuration includes slidably displacing the shield from a distal position to a proximal position. In some embodiments of the method 300, transitioning the shield from the safe configuration to the use configuration includes contacting the skin with the shield.

The method 400 may further include releasing a latch operatively coupled between the shield and the frame (block 430) to enable the shield to transition from the safe configuration to the use configuration.

The method 400 may further include distally sliding the skin nicking device along the needle toward the insertion site (block 440). In some embodiments of the method 300, distally sliding the skin nicking device may be preceded by decoupling a frame of the skin nicking device from a needle hub of the needle. In some embodiments of the method 300, distally sliding the skin nicking device may include distally displacing the skin nicking device so that the skin applies a proximally oriented force to the shield to displace the shield from the distal position toward the proximal position.

The method 400 may further include nicking the skin with the blade to enlarge the insertion site (block 450). In some embodiments of the method 300, nicking the skin includes distally sliding the skin nicking device along the needle so that the blade extends into the insertion site.

The method 400 may further include placing the catheter within the vasculature (block 460). The method 400 may further include transitioning the shield from the use configuration to the safe configuration (block 470) to encapsulate the blade.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter placement device, comprising:
a needle configured to establish an insertion site for a vascular catheter, the needle defining a needle lumen extending between a distal end and a needle hub at a proximal end; and
a skin nicking device slidably coupled with the needle, the skin nicking device comprising:
a blade configured to nick a skin adjacent the insertion site to enlarge the insertion site;
a shield transitionable between:
a safe configuration, wherein the blade is encapsulated by the shield, and
a use configuration, wherein the blade is exposed for use in nicking the skin;
a frame coupled with the blade and the shield; and
a latch operatively coupled between the shield and the frame, wherein the latch is configured to prevent shield from transitioning away from the safe configuration toward the use configuration in an absence of a deliberate action by a clinician.

2. The device according to claim 1, wherein the frame is coupled with the needle hub such that the frame is positionally retained by the needle hub in the absence of a separating force applied to the skin nicking device by the clinician.

3. The device according to claim 1, wherein the shield is rotatably coupled with the frame such that the shield is rotatable between the safe configuration and the use configuration.

4. The device according to claim 1, wherein the shield is slidably coupled with the frame such that the shield is displaceable between the safe configuration and the use configuration.

5. The device according to claim 4, wherein the shield is longitudinally displaceable between:
a distal position corresponding to the safe configuration, and
a proximal position corresponding to the use configuration.

6. The device according to claim 1, wherein the shield is biased toward the safe configuration.

7. The device according to claim 1, wherein the latch includes an actuator configured to release the latch as a result of the deliberate action, thereby allowing the shield to transition away from the safe configuration toward the use configuration.

8. The device according to claim 1, wherein the blade is fixedly attached to the frame such that the blade extends distally away from the frame.

9. The device according to claim 1, wherein:
the blade includes a sharp edge and a dull edge,
the sharp edge faces away from the dull edge, and the sharp edge is disposed at an angle with respect to the dull edge.

10. The device according to claim 9, wherein the sharp edge and the dull edge converge to define a sharp tip at a distal end of the blade.

11. The device according to claim 10, wherein the blade is fixedly attached to the frame such that:
the dull edge faces the needle,
the sharp edge faces radially away from the needle, and
the sharp tip is disposed immediately adjacent the needle.

12. The device according to claim 1, wherein:
the skin nicking device includes a tubular sheath coupled with the frame so that the tubular sheath extends distally away from the frame along the needle, and
the needle is disposed within a lumen of the tubular sheath.

13. The device according to claim 12, wherein a sharp tip is disposed radially inward of an outside diameter surface of the tubular sheath.

14. The device according to claim 12, wherein a sharp tip is embedded within a wall of the tubular sheath.

15. The device according to claim 1, wherein the skin nicking device includes a second blade fixedly coupled with the frame such that the second blade is disposed opposite the blade.

16. The device according to claim 15, wherein the shield is configured to:
encapsulate the second blade in the safe configuration, and
expose the second blade in the use configuration.

17. A method of placing a catheter within a patient vasculature, comprising:
accessing a blood vessel using a needle to define an insertion site for the catheter;
releasing a latch operatively coupled between a shield of a skin nicking device and a frame of the skin nicking device, wherein the latch is configured to prevent the shield from transitioning away from a safe configuration toward a use configuration in an absence of a deliberate action by a clinician;
transitioning the shield of the skin nicking device coupled with the needle from the safe configuration to the use configuration to expose a blade of the skin nicking device;
distally sliding the skin nicking device along the needle toward the insertion site;
nicking a skin with the blade to enlarge the insertion site; and
placing the catheter within the patient vasculature.

18. The method according to claim 17, wherein nicking the skin includes distally sliding the skin nicking device along the needle so that the blade extends into the insertion site.

19. The method according to claim 17, further comprising decoupling the frame of the skin nicking device from a needle hub of the needle.

20. The method according to claim 17, further comprising transitioning the shield from the use configuration to the safe configuration to encapsulate the blade.

21. The method according to claim 17, wherein transitioning the shield includes rotating the shield.

22. The method according to claim 17, wherein transitioning the shield from the safe configuration to the use configuration includes slidably displacing the shield from a distal position to a proximal position.

23. The method according to claim 22, wherein transitioning the shield from the safe configuration to the use configuration includes:

contacting the skin with the shield; and distally displacing the skin nicking device further along the needle so that the skin applies a proximally oriented force to the shield to displace the shield away from the distal position toward the proximal position.

* * * * *